(12) United States Patent
McGlinch et al.

(10) Patent No.: US 7,214,220 B2
(45) Date of Patent: May 8, 2007

(54) INTRAVASCULAR DEVICE WITH CARRIER TUBE ENGAGEMENT MEMBER

(75) Inventors: Timothy McGlinch, St. Paul, MN (US); Tim Mlsna, St. Michael, MN (US); Dean A. Peterson, Brooklyn Park, MN (US); David B. Robinson, Chanhassen, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1026 days.

(21) Appl. No.: 09/960,260

(22) Filed: Sep. 21, 2001

(65) Prior Publication Data
US 2003/0060803 A1   Mar. 27, 2003

(51) Int. Cl.
*A61M 25/16*   (2006.01)

(52) U.S. Cl. .................. 604/533; 604/103.05; 206/571

(58) Field of Classification Search ..............................
604/96.01–103.14, 93.01, 508, 509, 158, 604/161, 162, 246, 256, 264, 164.08, 523–539, 604/284, 915, 921; 607/116–120; 606/191–194; 600/585, 434, 435, 433; 206/570, 571, 363, 206/438
See application file for complete search history.

(56) References Cited

U.S. PATENT DOCUMENTS

| | | |
|---|---|---|
| 2,185,741 A | 1/1940 | Sorg et al. |
| RE25,788 E | 6/1965 | Sheridan |
| 3,318,335 A | 5/1967 | Heller |
| 3,348,544 A | 10/1967 | Braun |
| 3,470,869 A | 10/1969 | Fenton et al. |
| 3,720,210 A * | 3/1973 | Diettrich ..................... 604/533 |
| 3,725,522 A | 4/1973 | Sheridan et al. |
| 3,752,510 A | 8/1973 | Windischman et al. |
| 3,809,081 A | 5/1974 | Loveless |
| 3,861,972 A | 1/1975 | Glover et al. |
| 3,865,666 A | 2/1975 | Shoney |
| 3,873,391 A | 3/1975 | Plauka et al. |
| 3,914,002 A | 10/1975 | Berliner et al. |
| 3,950,052 A | 4/1976 | Walter et al. |
| 3,959,429 A | 5/1976 | Benning |
| 3,985,601 A | 10/1976 | Panagrossi |
| 3,989,571 A | 11/1976 | Harautuneian |
| 4,068,659 A | 1/1978 | Moorehead |
| 4,085,185 A | 4/1978 | Adair |
| 4,093,484 A | 6/1978 | Harrison et al. |
| 4,154,244 A | 5/1979 | Becker et al. |
| 4,171,943 A | 10/1979 | Tschanz et al. |
| 4,191,185 A | 3/1980 | Lemieux |
| 4,198,983 A | 4/1980 | Becker et al. |

(Continued)

FOREIGN PATENT DOCUMENTS

| | | |
|---|---|---|
| EP | 0 782 868 A1 | 7/1997 |

(Continued)

*Primary Examiner*—Nicholas D. Lucchesi
*Assistant Examiner*—Christopher D. Koharski
(74) *Attorney, Agent, or Firm*—Crompton, Seager & Tufte LLC (57) ABSTRACT

An intravascular device having an elongate shaft and a proximal hub assembly. The proximal hub assembly includes an interference fit member (IFM) which forms an interference fit with a carrier tube to reduce the tendency of the device to fall out of the carrier tube during handling and to provide for easy removal of the device when ready for use.

7 Claims, 12 Drawing Sheets

U.S. PATENT DOCUMENTS

| | | | |
|---|---|---|---|
| 4,207,900 A | 6/1980 | Patel et al. | |
| 4,210,478 A | 7/1980 | Shoney | |
| 4,284,459 A | 8/1981 | Patel et al. | |
| 4,328,056 A | 5/1982 | Snooks | |
| 4,354,495 A | 10/1982 | Bodicky | |
| 4,417,887 A | 11/1983 | Koshi | |
| 4,489,961 A | 12/1984 | Laidig | |
| 4,509,877 A | 4/1985 | Sobin et al. | |
| 4,511,163 A | 4/1985 | Harris et al. | |
| 4,607,746 A | 8/1986 | Stinnette | |
| 4,880,414 A * | 11/1989 | Whipple | 604/533 |
| 5,031,775 A | 7/1991 | Kane | |
| 5,059,174 A | 10/1991 | Vaillancourt | |
| 5,217,114 A * | 6/1993 | Gadberry et al. | 206/364 |
| 5,224,939 A * | 7/1993 | Holman et al. | 604/528 |
| 5,344,011 A | 9/1994 | DiBernardo et al. | |
| 5,366,444 A | 11/1994 | Martin | |
| 5,380,301 A * | 1/1995 | Prichard et al. | 604/533 |
| 5,524,757 A * | 6/1996 | Andrews et al. | 206/438 |
| 5,607,055 A | 3/1997 | Bettinger | |
| 5,810,867 A * | 9/1998 | Zarbatany et al. | 606/191 |
| 5,830,401 A | 11/1998 | Prichard et al. | |
| 5,843,048 A | 12/1998 | Gross | |
| 5,891,110 A * | 4/1999 | Larson et al. | 604/523 |
| 6,053,313 A * | 4/2000 | Farrell et al. | 206/364 |
| 6,068,121 A | 5/2000 | McGlinch | |
| 6,068,622 A | 5/2000 | Sater et al. | |
| 6,099,499 A * | 8/2000 | Ciamacco, Jr. | 604/103 |
| 6,113,576 A * | 9/2000 | Dance et al. | 604/164.01 |
| 6,228,073 B1 * | 5/2001 | Noone et al. | 604/533 |
| 6,273,404 B1 | 8/2001 | Holman et al. | |
| 6,491,681 B1 * | 12/2002 | Kunis et al. | 604/528 |
| 6,503,244 B2 * | 1/2003 | Hayman | 604/525 |
| 6,575,959 B1 * | 6/2003 | Sarge et al. | 604/533 |

FOREIGN PATENT DOCUMENTS

| | | |
|---|---|---|
| FR | 2.092.970 | 1/1972 |
| WO | WO 98/18515 | 5/1998 |

* cited by examiner

INTRAVASCULAR DEVICE WITH CARRIER TUBE ENGAGEMENT MEMBER

FIELD OF THE INVENTION

The present invention generally relates to medical devices and packaging methods therefor.

BACKGROUND OF THE INVENTION

Elongate intravascular devices such as balloon catheters and guide wires are often packaged in carrier tubes. A carrier tube provides a convenient way to package and handle an otherwise unwieldy intravascular device, but the intravascular device may have a tendency to fall out of the carrier tube. As such, there is an ongoing need to provide improved devices and packaging techniques to reduce this tendency.

SUMMARY OF THE INVENTION

To address this need, the present invention provides a number of alternative solutions. In one embodiment, for example, the present invention provides an intravascular device having an elongate shaft and a proximal hub assembly. The proximal hub assembly includes an interference fit member (IFM) which forms an interference fit with a carrier tube. The interference fit reduces the tendency of the device to fall out of the carrier tube during shipping and handling, but provides for easy removal of the device when it is ready for use.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
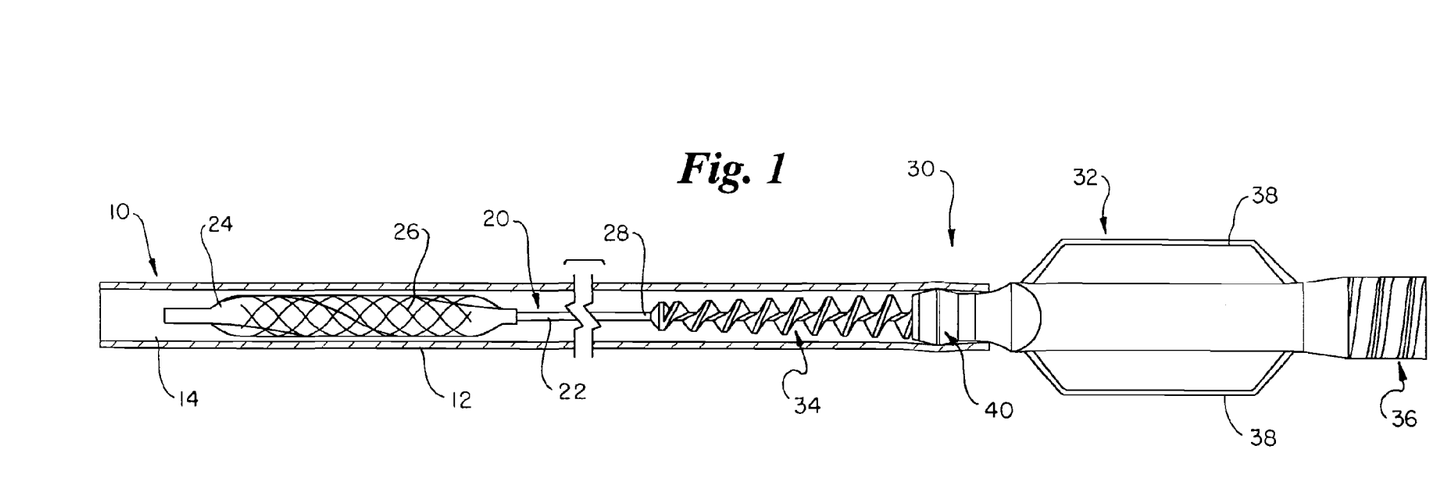
FIG. 1 is a partially cross-sectioned plan view of a catheter disposed in a carrier tube, wherein the catheter includes a single port hub assembly having a hub and an integral strain relief, with an IFM disposed on the hub, showing the IFM engaged with the inside surface of the carrier tube.

Refer now to FIG. 1 which illustrates a partially cross-sectioned plan view of a package 10 and an intravascular device 20 disposed therein. The package 10 includes a package wall 12 defining an elongate package lumen 14 therein. The package lumen 14 may be sized to accommodate substantially the entire length of the intravascular device 20 therein. The package lumen 14 may have an open proximal end and an open or closed distal end.

By way of example, not limitation, the package 10 is shown to be a carrier tube 10 having a carrier tube lumen 14 defined by a carrier tube wall 12. Carrier tube 10 may be formed utilizing conventional materials, dimensions and techniques. For example, the carrier tube 10 may be formed of an extruded polymer comprising a blend of 50% polyolefin copolymer available under the trade name SURLYN and 50% high density polyethylene, having an inside diameter ranging from 0.10 to 0.30 inches, a wall thickness ranging from 0.002 to 0.020 inches, and a length ranging from 12 to 72 inches. Other suitable polymers for the carrier tube 10 include thermoplastics such as fluoropolymers (PTFE, FEP, PFA, CTFE), nylons, phenylene oxides, polyesters, polyethylenes, polypropylene, polyurethanes, combinations thereof, blends thereof, etc.

Intravascular device 20 is removably disposed in the lumen 14 of the carrier tube 10. Intravascular device 20 generically refers to a wide variety of elongate intravascular devices such as catheters and guide wires. For example, the intravascular device may comprise a balloon catheter, a guide catheter, a diagnostic catheter, a guide wire, a drug delivery catheter, an atherectomy catheter, a tubular sheath, a stent delivery catheter, etc.

For purposes of illustration only, intravascular device 20 is shown in the form of an intravascular balloon catheter 20 having an elongate shaft 22, a distally mounted balloon 24 and a stent 26 disposed thereon. A proximal portion 28 of the elongate shaft 2 is connected to a hub assembly 30.

Hub assembly 30 includes a hub portion 32 and a strain relief 34. The proximal portion 28 of the elongate shaft 22 extends through the strain relief 34 and into the hub 32. The hub assembly 30 may be adhesively or thermally bonded to the proximal shaft portion 28. Alternatively, the proximal portion 28 of the elongate shaft 22 may be connected to the hub assembly by an insert molding technique. As a further alternative, the hub assembly 32 may be removably connected to the proximal shaft portion 28 utilizing a releasable compression fitting.

The hub 32 and the strain relief 34 may be a two-piece construction or a one-piece construction as shown. Examples of one-piece and two-piece constructions are described in U.S. Pat. No. 6,273,404 B1 to Holman et al, the entire disclosure of which is incorporated herein by reference. In one-piece constructions, the hub 32 and the strain relief 34 may be formed of the same material, such as polycarbonate. Other moldable polymeric material having sufficient impact resistance and chemical resistance may be utilized as well. In two-piece constructions, the hub 32 and the strain relief 34 may be formed of two different materials. For example, the hub may be formed of polycarbonate, and the strain relief may be formed of a relatively less rigid polymer such as polyurethane available under the trade name PELLETHANE.

The strain relief 34 reduces the tendency of the proximal shaft portion 28 to kink just distal of the hub 32. Typically, the hub 32 is relatively stiff and rigid, whereas the shaft 22/28 is relatively flexible, which may create a stress concentration point therebetween, absent the strain relief 34. Thus, the strain relief 34 provides a gradual transition in stiffness between the hub 32 and the proximal shaft portion 28. In this particular embodiment, the strain relief 34 has a helical shape and a gradual reduction in profile, as described by Holman et al., to provide such a transition in stiffness.

In this particular embodiment, the hub 32 includes a single port fluid connector 36 for connection to an ancillary device such as an inflation device (not shown). The hub 32 may incorporate more than one connector 36, or no connector at all, depending on the type of intravascular device 20 utilized. For example, an otherwise conventional guide wire may not require a fluid connector 36, whereas an otherwise conventional over-the-wire (OTW) type balloon catheter may require a double port connector 36.

Also in this particular embodiment, the hub assembly 30 includes a pair of wings 38 to facilitate easier handling and manipulation of the catheter 20. The particular shape of the wings 38 may vary, depending on the manipulation requirements of the device 20. In some instances, wings 38 may not be necessary or desirable.

The hub assembly 30 includes an interference fit member (IFM) 40 connected to a distal portion of the hub 32, proximal of the strain relief 34. The IFM 40 may be connected to any portion of the hub assembly 30, or to any portion of the proximal shaft 28. The IFM 40 may form an interference fit with any portion the carrier tube 10, such as the inside surface of the carrier tube wall 12 as shown in FIG. 1.

As seen in FIG. 1, the carrier tube wall 12 and/or the IFM 40 has sufficient compressibility to deform and thereby permit the IFM 40 to enter into the carrier tube lumen 14 despite the nominal difference in size. The interference fit between the IFM 40 and the carrier tube 10 establishes sufficient friction to resist gravitational and handling forces which may otherwise cause the device 20 to fall out of the carrier tube 10. The friction created by the interference fit may also be sufficiently small to permit easy removal of the device 20 from the carrier tube 10 as shown in FIG. 2.

The IFM 40 may be sized and shaped to be fully or partially disposed inside the carrier tube lumen 14. By fully extending the IFM 40 into the carrier tube lumen 14 a distance from the proximal end of the carrier tube 10, the IFM 40 is less likely to be accidentally dislodged by rough handling or the like. To this end, the IFM 40 may establish a contact surface area with the inside surface of the carrier tube wall 14 that is distal of the proximal end of the carrier tube 10.

Figure 2:
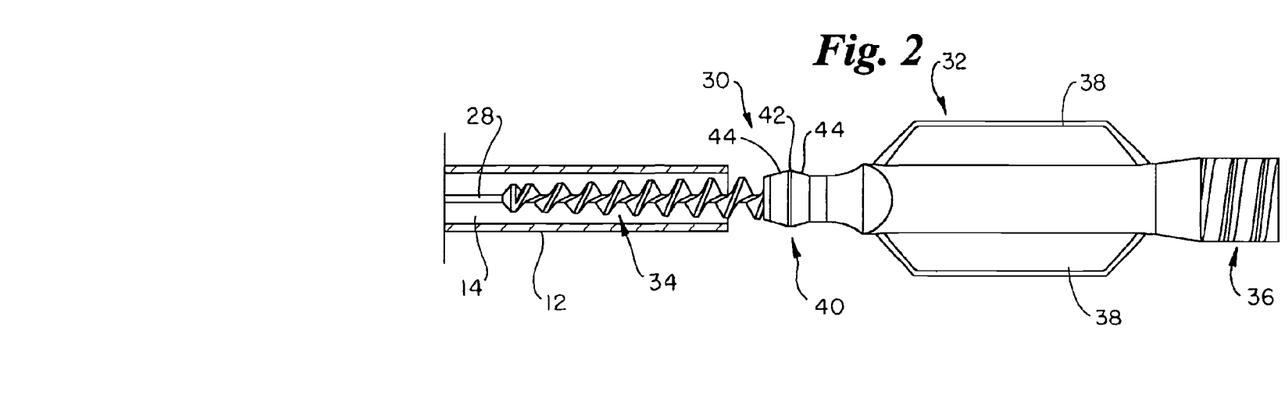
FIG. 2 is a partially cross-sectioned view of a proximal portion of the carrier tube and the catheter illustrated in FIG. 1, showing the IFM disengaged from the carrier tube.
Figure 2A:
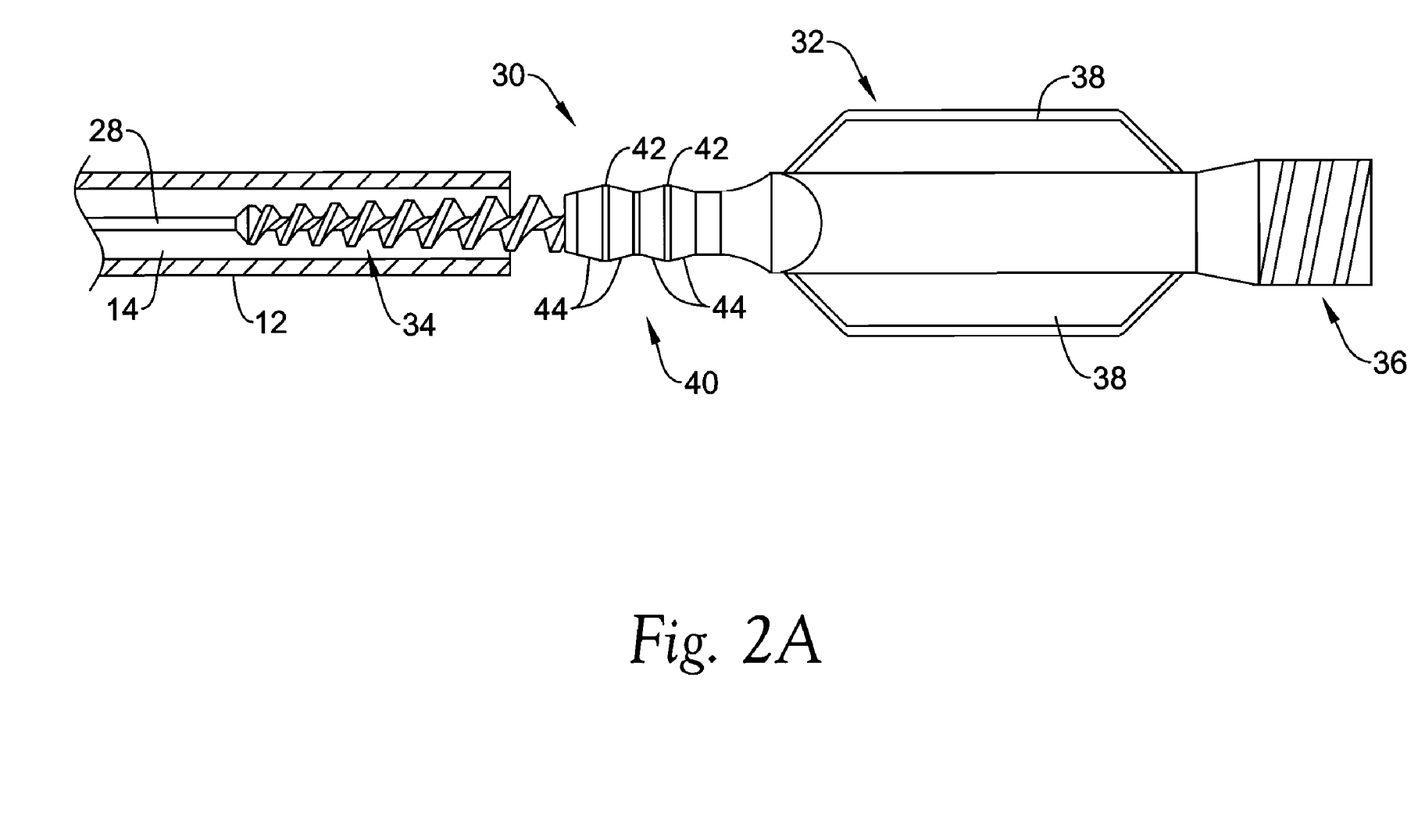
FIG. 2A is an embodiment similar to that shown in FIGS. 1 and 2 where the IFM has more than one ring.

In the embodiment illustrated in FIGS. 1 and 2, the IFM 40 comprises a ring having middle portion 42 and end portions 44. End portions 44 may be tapered and may have a diameter or profile that is less than the diameter or profile of the middle portion 42. The middle portion 42 may have a diameter or profile that is greater than the inside diameter or inside profile of the carrier tube 10 adjacent the proximal end thereof. For example, the middle portion 42 may have a diameter or profile that is 0.0005 to 0.010 inches greater than the inside diameter or inside profile of the carrier tube 10. Also by way of example, if the inside diameter of the carrier tube 10 is approximately 0.17 to 0.18 inches, the middle portion 42 may have a diameter of approximately 0.181 to 0.187 inches. In some embodiments, as shown in FIG. 2A. the IFM 40 can comprise more than one ring.

The remaining FIGS. 3–15 described herein illustrate variations of the hub assembly 30 and IFM 40. Except as described and evident from the drawings, the principles of design, function, use and manufacture may be the same as described previously. To this end, similar elements may be numbered the same or have the same last two digits.

Figure 3:
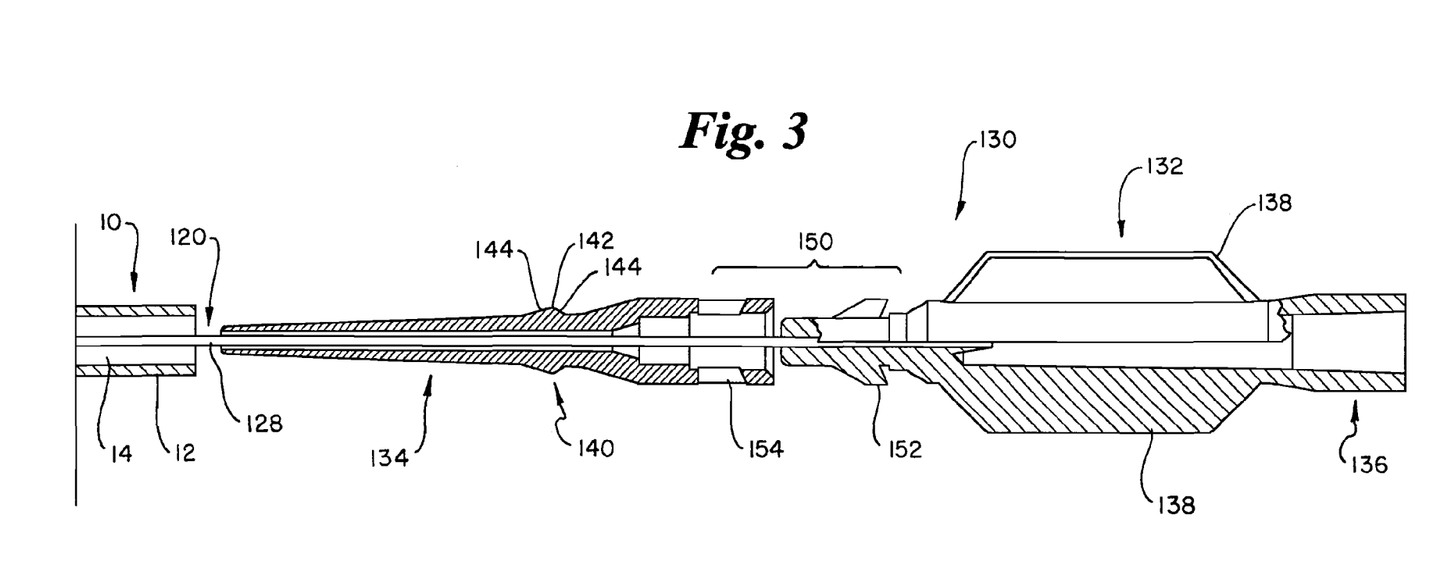
FIG. 3 is a partially cross-sectioned exploded view of a proximal portion of a carrier tube and an alternative catheter, wherein the catheter includes a hub assembly having a hub and a snap-fit strain relief, with an IFM disposed on the strain relief.

Refer now to FIG. 3 which illustrates a partially cross-sectioned exploded view of the proximal portion of the carrier tube 10 and an alternative catheter 120. The catheter 120 includes a hub assembly 130 having a hub 132 and a snap-fit strain relief 134. The snap-fit strain relief 134 may be connected to the hub 132 utilizing a mechanical lock 150. Mechanical lock 150 includes mating parts 152/154 which permit the strain relief 134 to be easily snap-fit onto the hub 132 to establish a rigid connection therebetween, as described by Holman et al.

Figure 4:
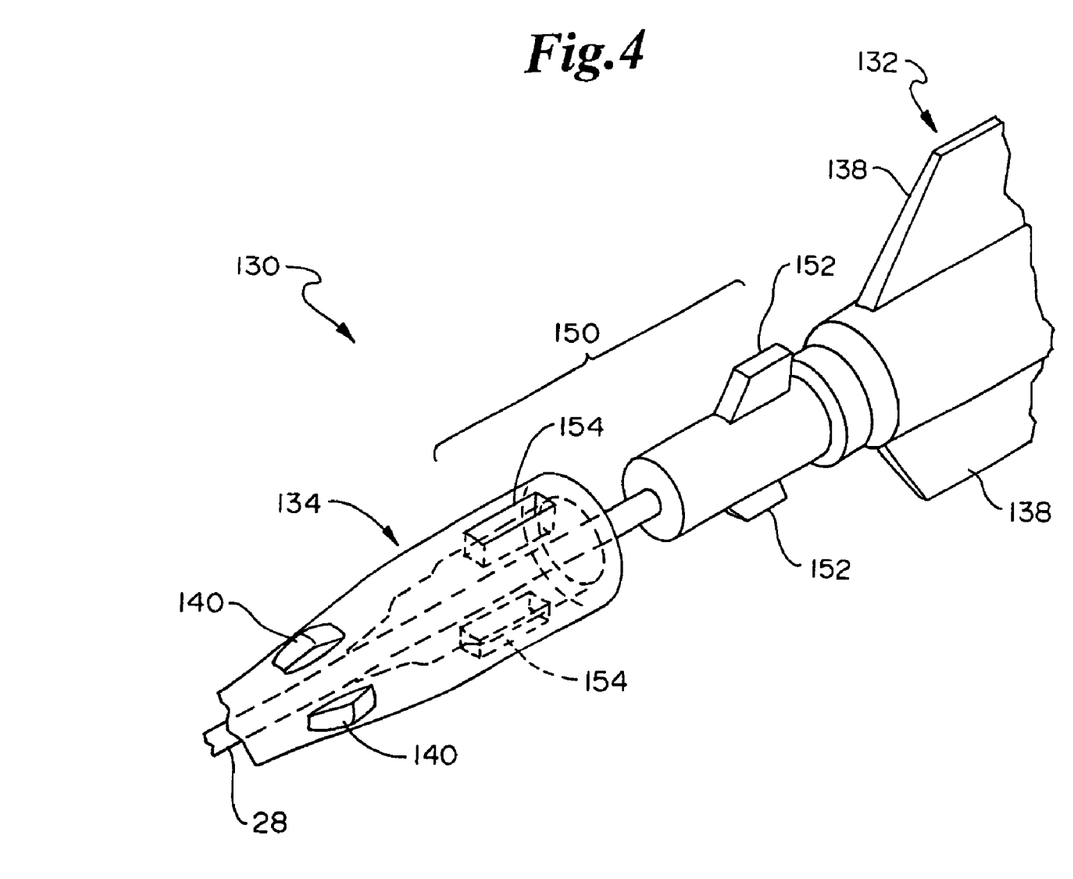
FIG. 4 is an exploded isometric view of the catheter illustrated in FIG. 3.

An IFM 140 is disposed on the strain relief 134. The IFM 140 may comprise a circular ring as shown in FIG. 2 or a plurality of protrusions distributed about the circumference of the strain relief 134 as illustrated in FIG. 4. The IFM 140 includes a middle portion 142 and tapered end portions 144. Middle portion 142 establishes an interference fit with the inside surface of the carrier tube wall 12.

Figure 5:
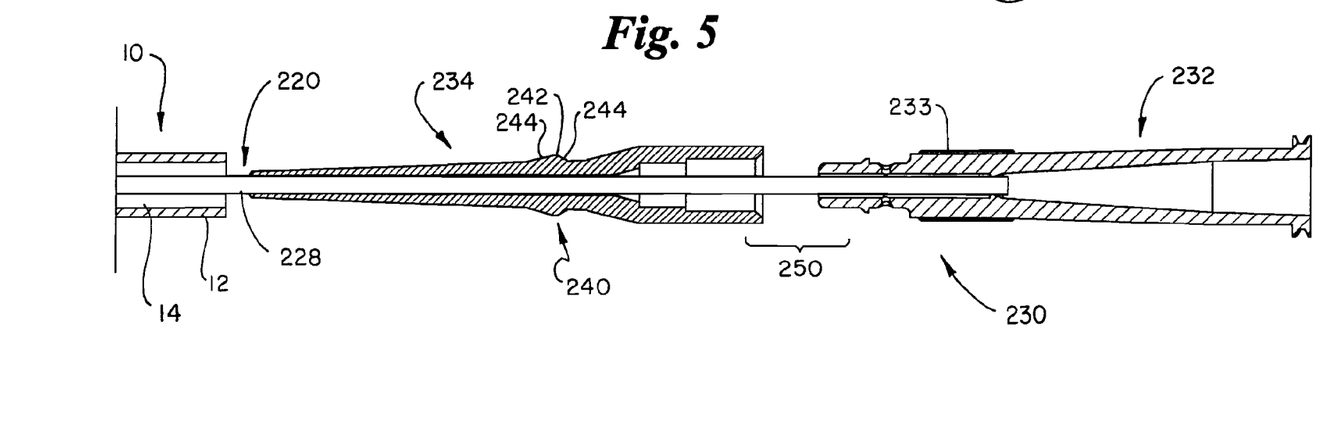
FIG. 5 is a partially cross-sectioned exploded view of a proximal portion of a carrier tube and an alternative catheter, wherein the catheter includes a hub assembly having a hub with a plurality of grip protrusions and a snap-fit strain relief, with an IFM disposed on the strain relief.
Figure 6:
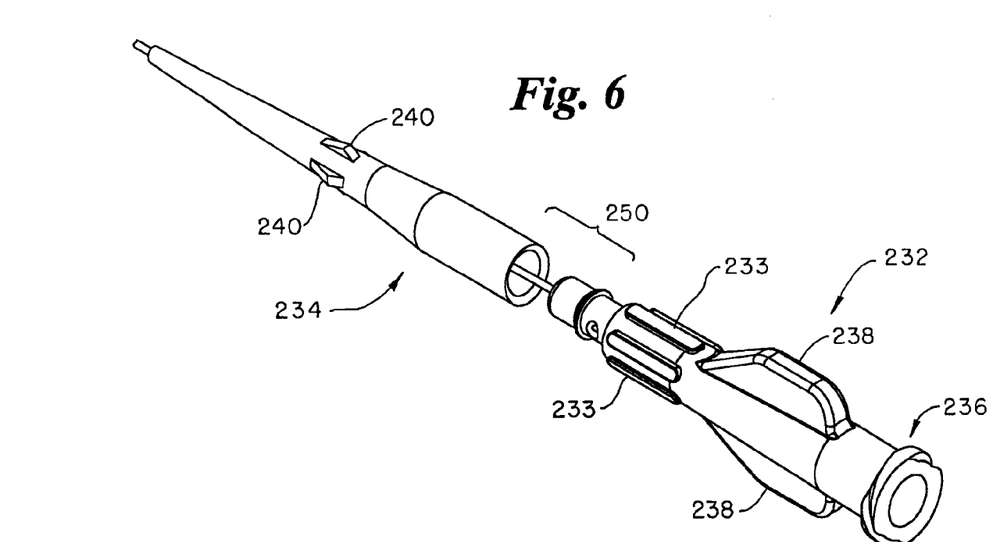
FIG. 6 is an exploded isometric view of the catheter illustrated in FIG. 5.

Refer now to FIG. 5 which illustrates a partially cross-sectioned exploded view of the proximal portion of the carrier tube 10 and an alternative catheter 220 disposed therein. The catheter 220 includes a hub assembly 230 having a hub 232 and a snap-fit strain relief 234. The strain relief 234 may be connected to the hub 232 by a mechanical lock 250 as described by Holman et al. Hub 232 also includes a plurality of grip protrusions 233 disposed about the circumference of the hub 232 proximal of the strain relief 234 and distal of the wings 238 as best seen in FIG. 6. Grip protrusions 233 enhance the ability of the physician to grip the hub assembly 230 to manipulate the catheter 220.

An IFM 240 is disposed on the strain relief 234. The IFM 240 may comprise a circular ring as illustrated in FIG. 2 or a plurality of protrusions distributed about the circumference of the strain relief 234 as shown in FIG. 6. The IFM 240 includes a middle portion 242 and tapered end portions 244. The middle portion 242 forms an interference fit with the inside surface of the carrier tube wall 12.

Figure 7:
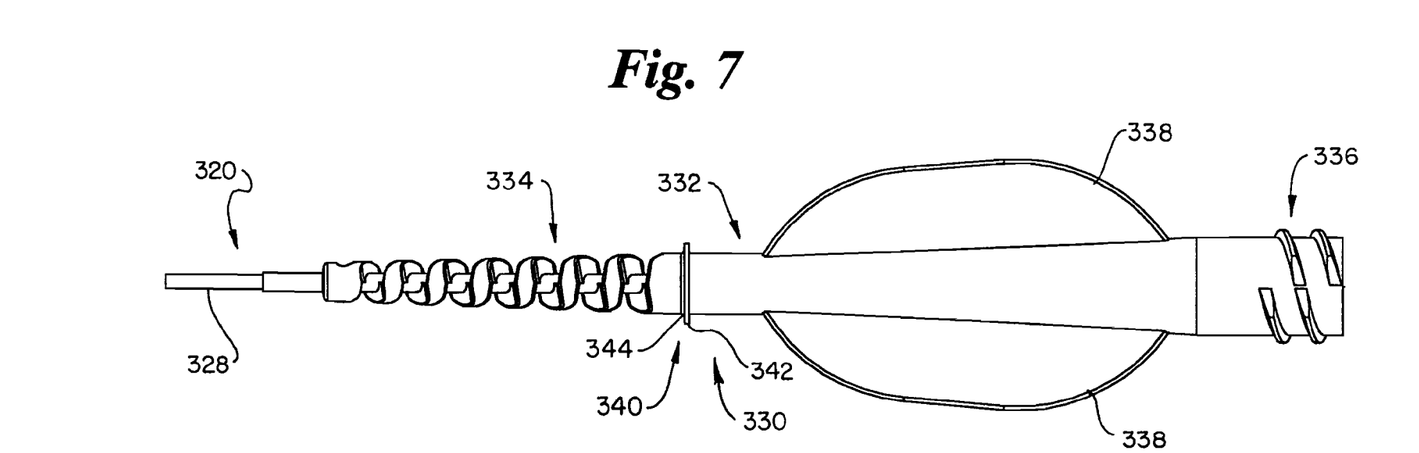
FIG. 7 is a plan view of a proximal portion of an alternative catheter, wherein the catheter includes a hub assembly having a hub and an integral strain relief, with an IFM disposed on the hub.

Refer now to FIG. 7 which illustrates a plan view of a proximal portion of an alternative catheter 320. Catheter 320 includes a hub assembly 330 having a hub 332 and an integral strain relief 334. An IFM 340 is disposed on the hub 332 just proximal of the strain relief 334. The IFM 340 comprises a thin ring having a middle portion 342 and a tapered proximal portion 344. The middle portion 342 engages the inside surface of the carrier tube wall 12 (not shown) to form an interference fit therebetween.

Figure 8:
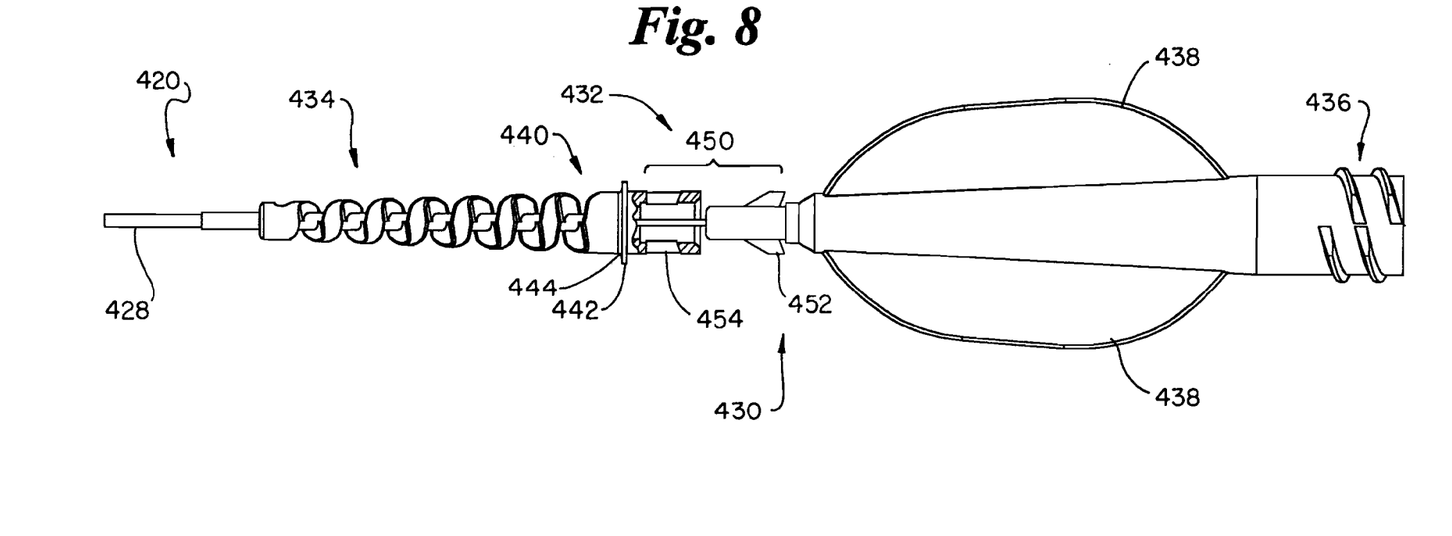
FIG. 8 is a plan view of a proximal portion of an alternative catheter, wherein the catheter includes a hub assembly having a hub and a snap-fit strain relief, with an IFM disposed on the strain relief.

Refer now to FIG. 8 which illustrates a plan view of a proximal portion of an alternative catheter 420. The catheter 420 includes a hub assembly 430 having a hub 432 and a snap-fit strain relief 434. A mechanical lock 450 having mating members 452/454 mechanically connects the hub 432 to the strain relief 434 as described by Holman et al. An IFM 440 is disposed on a proximal portion of the strain relief 434. The IFM 440 comprises a circular ring having a middle portion 442 and a proximal tapered portion 444. The middle portion 442 of the IFM 440 engages the inside surface of the carrier tube wall 12 (not shown) to form an interference fit therebetween.

Figure 9:
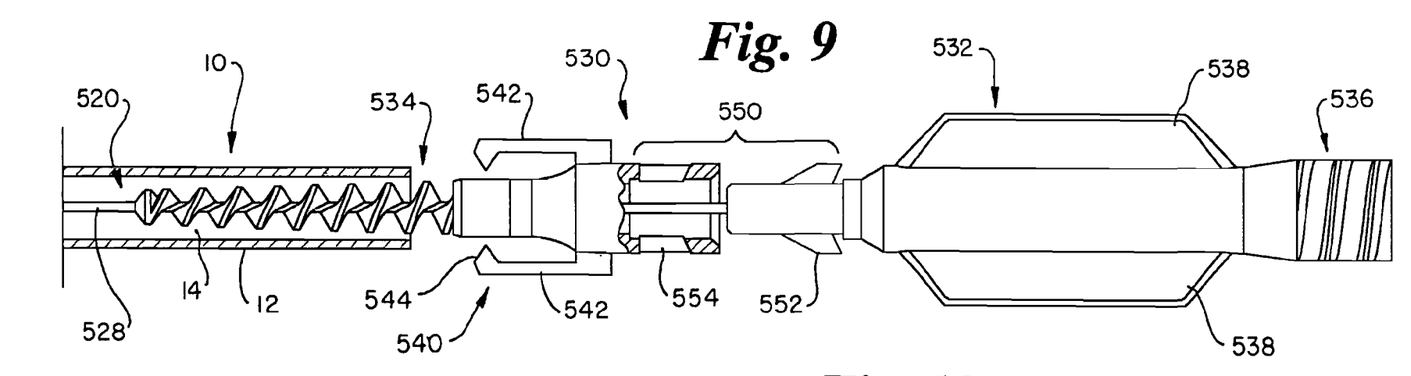
FIG. 9 is an exploded view of a proximal portion of a carrier tube and an alternative catheter, wherein the catheter includes a hub assembly having a hub and a snap-fit strain relief, with an IFM disposed on the strain relief, showing the IFM disengaged from the outside surface of the carrier tube.

Refer now to FIG. 9 which illustrates an exploded view of the proximal portion of the carrier tube 10 and an alternative catheter 520 disposed therein. Catheter 520 includes a hub assembly 530 having a hub 532 and a snap-fit strain relief 534. The hub 532 may be connected to the strain relief 534 by a mechanical connection 550 having mating elements 552/554 as described by Holman et al.

An IFM 540 is connected to the strain relief 534 distal of the mechanical connection 550. The IFM 540 includes a pair of opposing flexure arms 542 each having one or more teeth 544. Flexure arms 542 may bias the teeth 544 against the outside surface of the carrier tube wall 12. The teeth 544 form an interference fit with the outside surface of the carrier tube wall 12.

Figure 10:
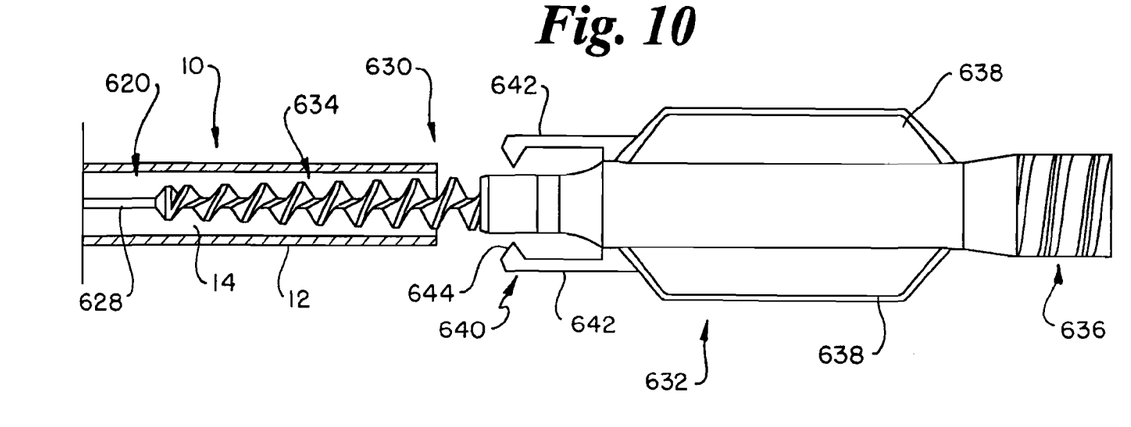
FIG. 10 is a plan view of a proximal portion of a carrier tube and an alternative catheter, wherein the catheter includes a hub assembly having a hub and an integral strain relief, with an IFM disposed on the hub, showing the IFM disengaged from the outside surface of the carrier tube.

Refer now to FIG. 10 which illustrates a plan view of the proximal portion of the carrier tube 10 and an alternative catheter 620 disposed therein. The catheter 620 includes a hub assembly 630 having a hub 632 and an integral strain relief 634. An IFM 640 is disposed on the hub 632 proximal of the strain relief 634. The IFM 640 includes a pair of opposing flexure arms 642, each having one or more teeth 644. Flexure arms 642 bias the teeth 644 against the outside surface of the carrier tube wall 12 to establish an interference fit therebetween.

Refer now to FIGS. 11–15 which illustrate isometric views of the proximal portion of the carrier tube 10 and alternative designs of a catheter 720 having a double port hub assembly 730. The double port hub assembly 730 is particularly suitable for over the wire (OTW) type balloon catheters. The hub assembly 730 includes a pair of port connectors 736.

In each of the embodiments illustrated in FIGS. 11–15, the hub assembly 730 includes a hub portion 732 and a strain relief portion 734. Also in each of the embodiments illustrated in FIGS. 11–15, an IFM 740 in the form of a plurality of protrusions is disposed on a portion of the hub assembly 730. Each of the protrusions 740 includes a middle portion 742 and tapered end portions 744. The middle portion 742 forms an interference fit with the inside surface of the carrier tube wall 12.

Figure 11:
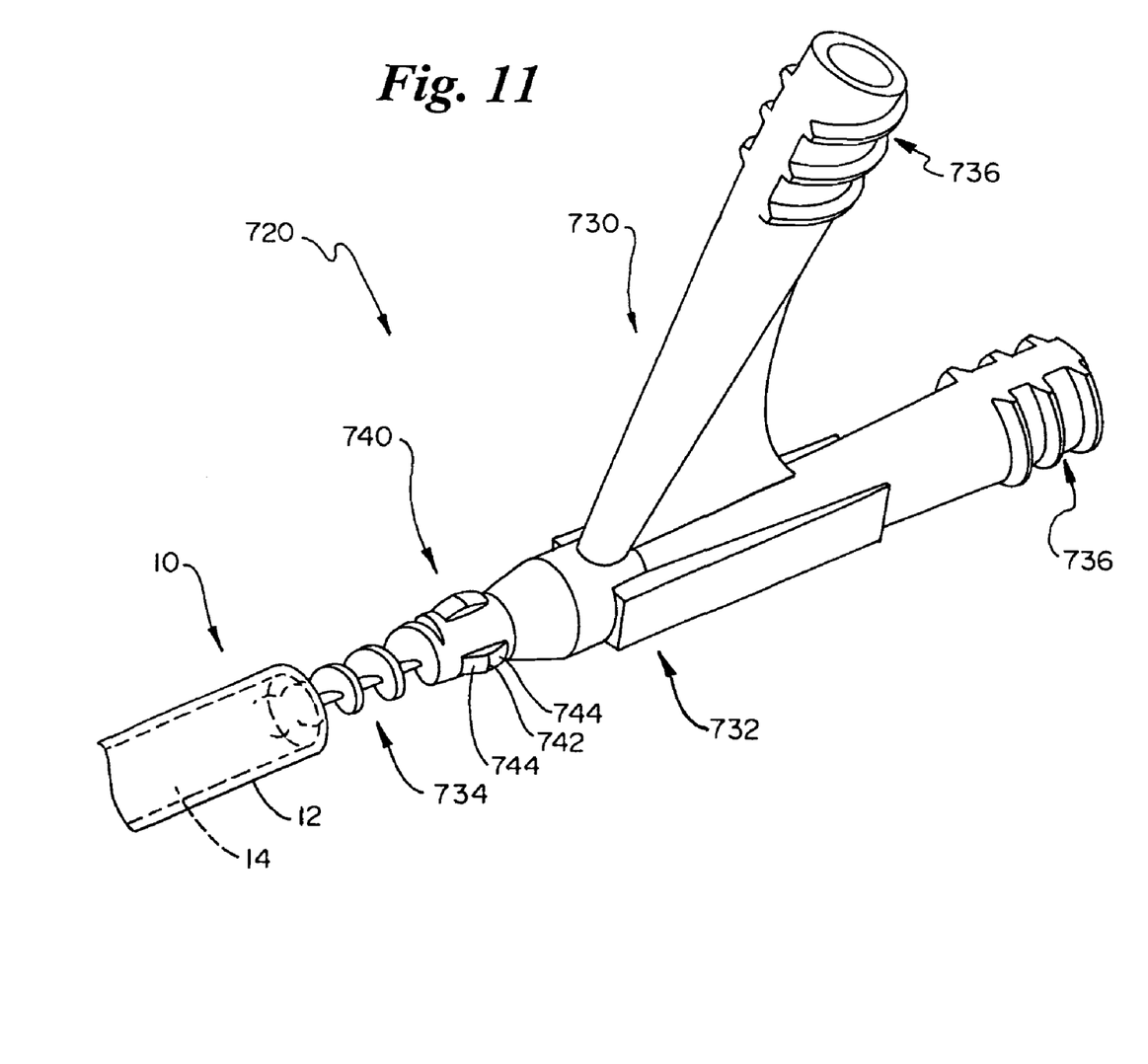
FIGS. 11–15 are isometric views of a proximal portion of a carrier tube and alternative catheter designs, each with an IFM disposed on a double port hub assembly.
Figure 12:
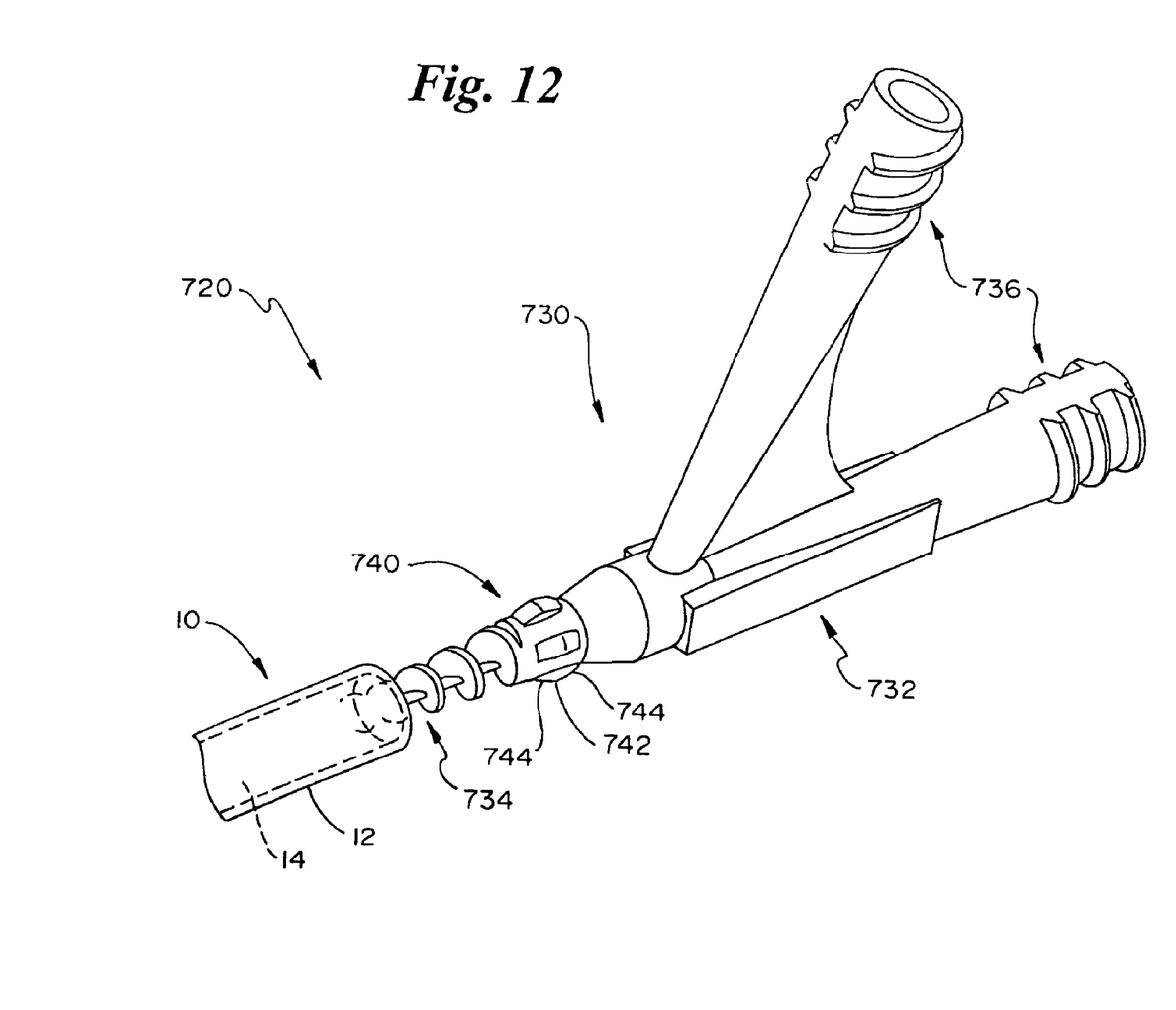

In the embodiments illustrated in FIGS. 11 and 12, the hub 732 and the strain relief 734 are integrally formed as described by Holman et al. In the embodiments illustrated in FIGS. 13–15, the hub 732 and the strain relief 734 comprise a two-piece construction that may be snap-fit together using a mechanical connection 750 including mating members 752 and 754 as described by Holman et al.

Figure 15:
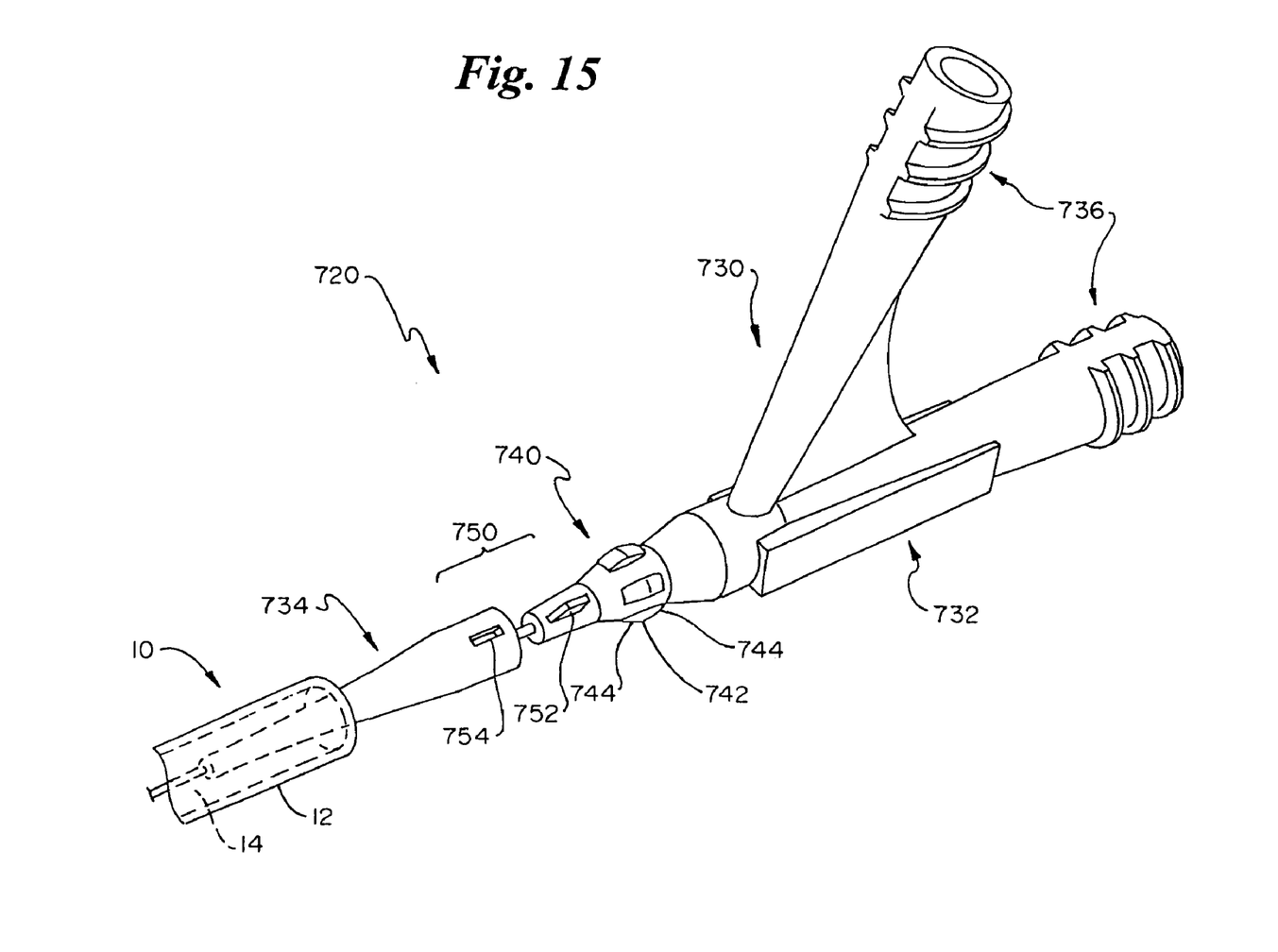

In the embodiments described in FIGS. 11, 12 and 15, the IFM 740 is disposed on a distal portion of the hub 732. In the embodiments illustrated in FIGS. 13 and 14, the IFM 740 is disposed on the strain relief 734.

Figure 13:
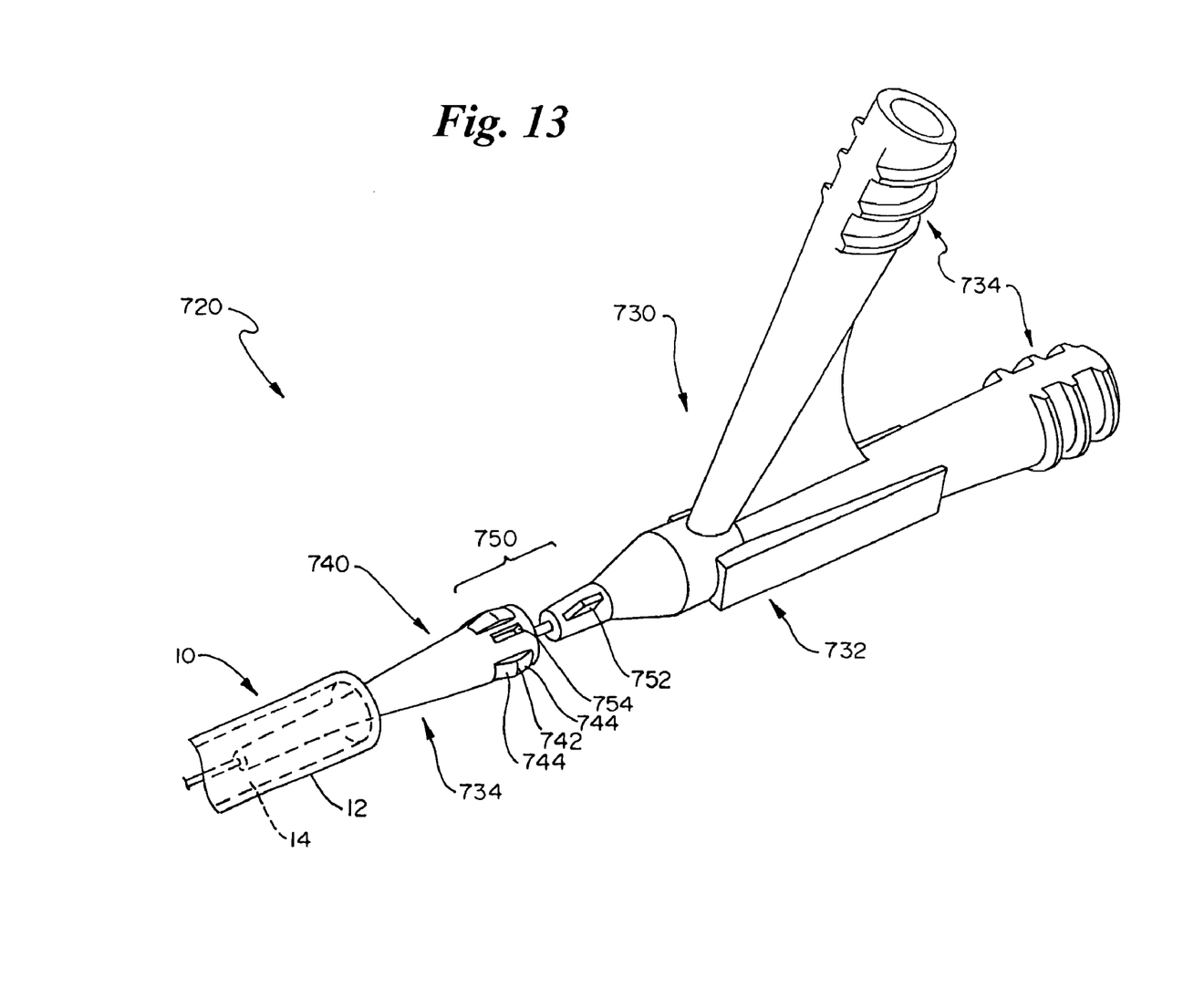
Figure 14:
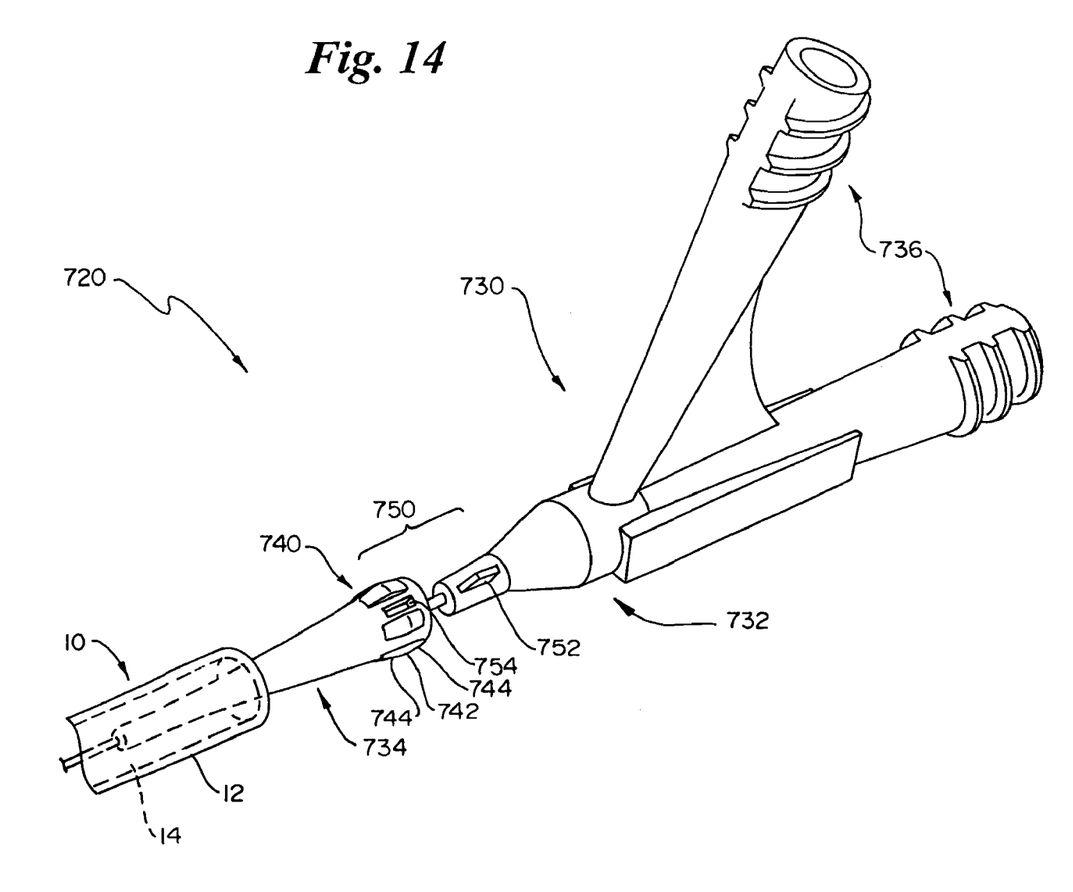

In the embodiments illustrated in FIGS. 11 and 13, the IFM 740 comprises four protrusions distributed about the circumference of hub assembly 730 spaced apart by approximately 90 degrees. In the embodiments illustrated in FIGS. 12, 14 and 15, the IFM 740 comprises six protrusions spaced approximately 60 degrees apart about the circumference of the hub assembly 730.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular device suitable for packaging in a package lumen defined by a package lumen wall, the intravascular device comprising:
   an elongate shaft having a proximal portion; and
   a hub assembly connected to the proximal portion of the elongate shaft, the hub assembly including an interference fit member (IFM) which is configured to form an interference fit with the package lumen wall when the intravascular device is disposed in the package lumen;
   wherein the interference fit establishes sufficient friction to resist gravitational and handling forces which may otherwise cause the intravascular device to fall out of the package lumen;
   wherein the friction created by the interference fit is sufficiently small to permit easy removal of the intravascular device from the package lumen; and
   wherein the IFM comprises one or more rings.

2. An intravascular device as in claim 1, wherein the one or more rings has a middle portion and a distal end portion and a proximal end portion.

3. An intravascular device as in claim 2, wherein the middle portion of the ring has a larger diameter than the end portions.

4. An intravascular device as in claim 2, wherein the end portions taper from the diameter of the middle portion to a smaller diameter than the middle portion.

5. An intravascular device as in claim 1, wherein the one or more rings has a middle portion and a proximal tapered portion.

6. An intravascular device suitable for packaging in a package lumen defined by a package lumen wall, the intravascular device comprising:
   an elongate shaft having a proximal portion; and a hub assembly connected to the proximal portion of the elongate shaft, the hub assembly including an interference fit member (IFM) which is configured to form an interference fit with the package lumen wall when the intravascular device is disposed in the package lumen;
   wherein an inner diameter of the package lumen wall is smaller than the outer diameter of the IFM such that the IFM deforms the package lumen wall when the IFM is in an interference fit with the package lumen wall; and
   wherein the IFM causes the package lumen wall to bulge outwardly when the IFM is disposed within the package lumen wall.

7. An intravascular device suitable for packaging in a package lumen defined by a package lumen wall, the intravascular device comprising:
   an elongate shaft having a proximal portion; and
   a hub assembly connected to the proximal portion of the elongate shaft, the hub assembly including an interference fit member (IFM) which is configured to form an interference fit with the package lumen wall when the intravascular device is disposed in the package lumen;

wherein the interference fit establishes sufficient friction to resist gravitational and handling forces which may otherwise cause the intravascular device to fall out of the package lumen;

wherein the friction created by the interference fit is sufficiently small to permit easy removal of the intravascular device from the package lumen;

wherein the hub assembly includes a hub and a strain relief, and wherein the IFM is carried by the hub; and wherein the IFM is disposed on a distal end of the hub, proximal the strain relief.

* * * * *